United States Patent [19]

Anderson

[11] Patent Number: 5,408,306
[45] Date of Patent: Apr. 18, 1995

[54] ROTATING DISK ELECTRODE METHOD AND APPARATUS FOR MULTI-ELEMENTAL DETERMINATION OF CONCENTRATION OF PARTICLES IN USED OIL

[75] Inventor: Daniel P. Anderson, Stoneham, Mass.

[73] Assignee: Spectro Incorporated, Littleton, Mass.

[21] Appl. No.: 197,360

[22] Filed: Feb. 16, 1994

Related U.S. Application Data

[63] Continuation-in-part of Ser. No. 876,874, May 1, 1992, abandoned.

[51] Int. Cl.⁶ .............................................. G01N 1/00
[52] U.S. Cl. ..................................... 356/36; 356/313; 422/101; 436/177
[58] Field of Search ................... 356/36, 313; 422/101; 436/177

[56] References Cited

U.S. PATENT DOCUMENTS

| | | | |
|---|---|---|---|
| 2,920,201 | 1/1960 | Annis et al. | 250/49.5 |
| 3,526,127 | 9/1970 | Sarkis | 73/64 |
| 3,583,812 | 6/1971 | Blum et al. | 356/86 |
| 3,736,059 | 5/1973 | Schuhknecht et al. | 356/86 |
| 3,981,584 | 9/1976 | Guymer | 356/70 |
| 3,981,585 | 9/1976 | Belcher et al. | 356/36 X |
| 4,047,814 | 9/1977 | Westcott | 356/38 |
| 4,176,545 | 12/1979 | Oddo | 73/64 |
| 4,448,887 | 5/1984 | Kauffman et al. | 436/60 |
| 4,492,461 | 1/1985 | Jones et al. | 356/38 |
| 4,789,526 | 12/1988 | Matkovich | 422/101 |

Primary Examiner—James C. Housel
Assistant Examiner—Long V. Le
Attorney, Agent, or Firm—James E. Maslow

[57] ABSTRACT

Spectrometric analysis for determining the elemental concentration of various wear metals, contaminants and additives present in a fluid sample for condition monitoring and preventive maintenance. RDE spectroscopy method and apparatus includes use of rotrode disk as a filter which captures large particles of the surface of the disk, which particles are then subjected to RDE spectroscopy for evaluation. In one method, the rotrode with the captured large-particle filtrate is subjected to a solvent wash, and the washed sample is then submitted to RDE spectroscopy to obtain a highly accurate multi-elemental determination of concentration of large particles. In another method, conventional RDE spectroscopy is used to characterize the small particles in a used oil sample, and this is combined with the obtained large particle data for highly accurate multi-elemental determination of concentration of wear debris, contaminants and additives in the fluid sample.

13 Claims, 3 Drawing Sheets

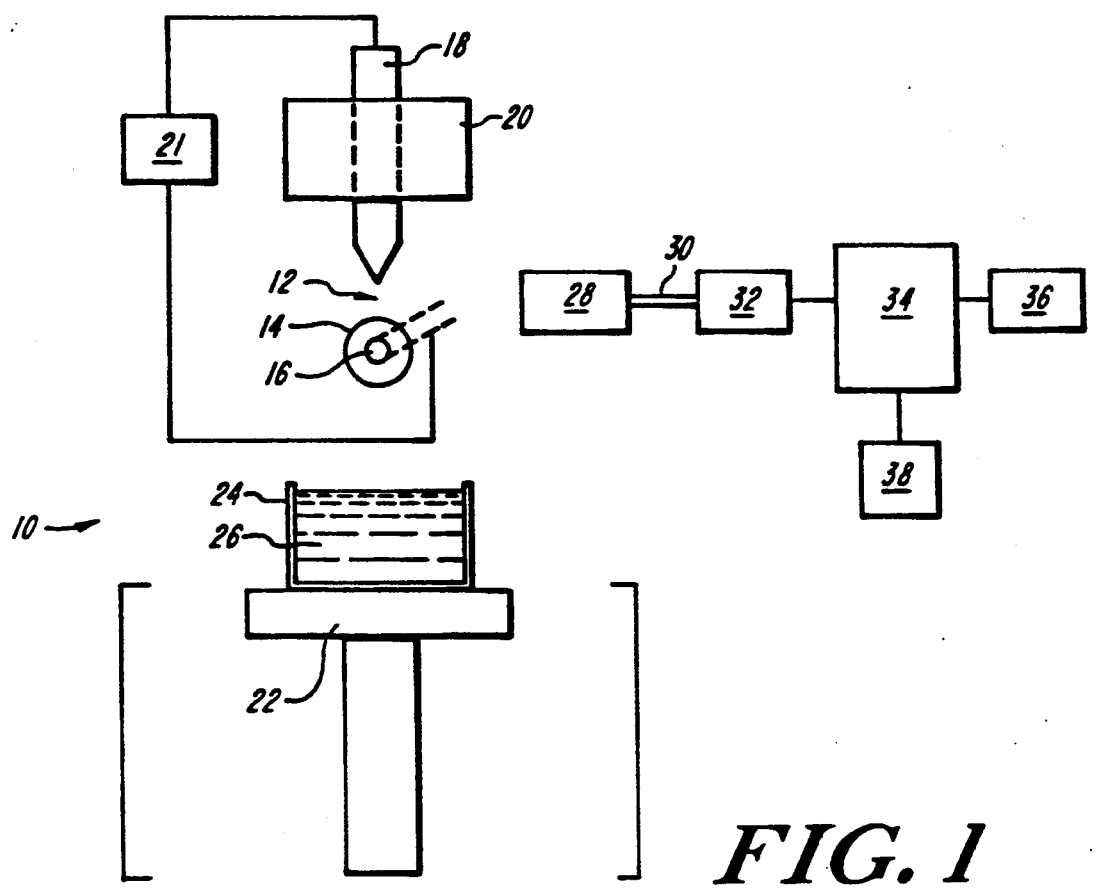
FIG. 1
FIG. 2
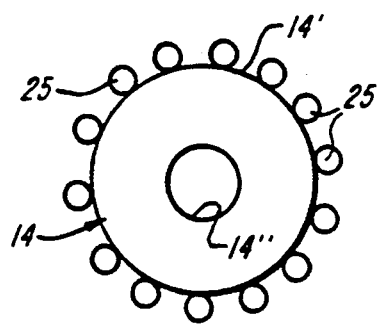

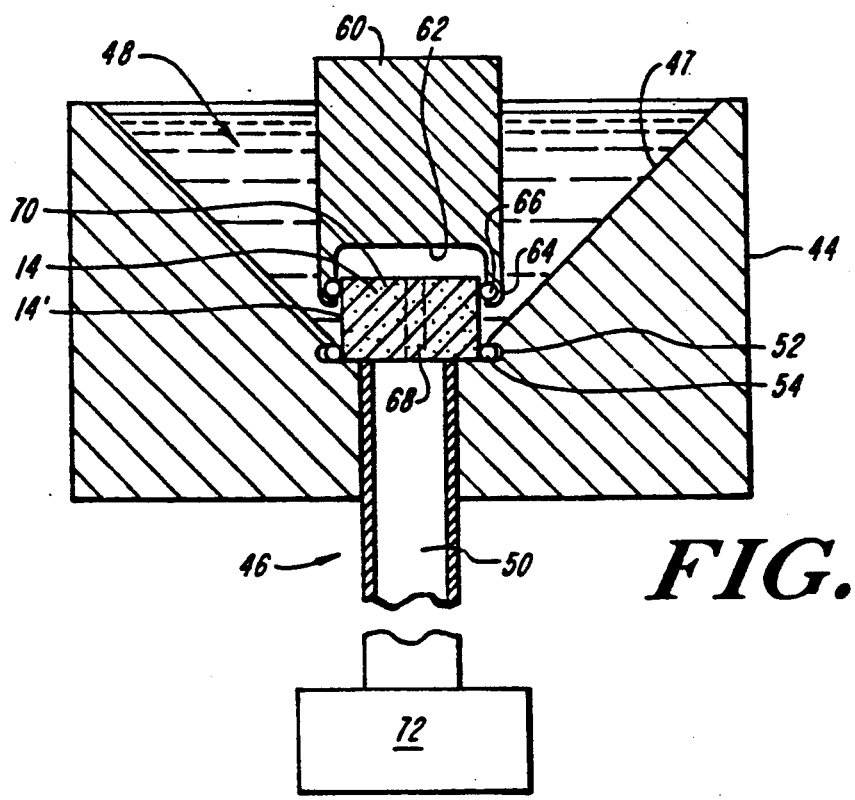
FIG. 3
FIG. 4
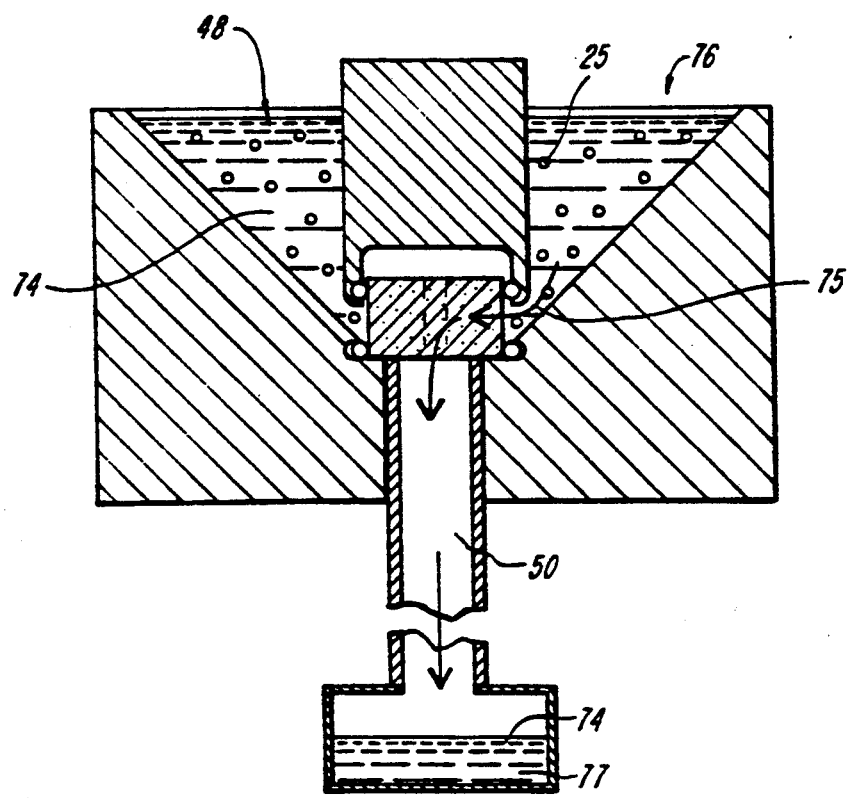

ROTATING DISK ELECTRODE METHOD AND APPARATUS FOR MULTI-ELEMENTAL DETERMINATION OF CONCENTRATION OF PARTICLES IN USED OIL

This is a continuation-in-part of application Ser. No. 07/876,874, filed May 1, 1992 now abandoned.

BACKGROUND OF THE INVENTION

The present invention relates to spectroscopy, and more particularly, to rotating disk electrode spectroscopy.

One common method of spectrometric oil analysis involves use of optical emission spectroscopy for detecting and quantifying the presence of elements in the tested sample. Optical emission spectroscopy is based on the fact that each element has a unique atomic structure. When subjected to the addition of energy, each element emits light at characteristic wavelength(s), which emission is seen as spectral lines and are a unique signature for such element. The intensity of the emitted light is proportional to the quantity of the element present in the sample. Thus the presence and quantity of the element can be detected and indicated. If non-conflicting signatures are selected for a plurality of elements, then a plurality of elements can be detected in a single test.

The typical optical emission spectrometer includes a sample of oil input, an excitation source for exciting the elements in the sample into a transmission state, an optical system to isolate emissions into discrete wavelengths, and a readout system. The typical excitation source is an electric discharge, in the form of an arc or spark. Energy from the source is imparted to the sample. Typically, two electrodes form a capacitatively-driven spark gap and the oil is carried into the gap. Upon discharge, a portion of the oil is rapidly heated and vaporizes into a plasma, i.e., a hot, highly ionized gas which emits intense light. The light given off as a result of this energization contains emissions from all of the elements in the sample. The optical system identifies individual signature spectra and the readout communicates the identified spectra and the intensity thereof.

For some condition monitoring applications, such as for reciprocating engines, in which abnormal wear often tends to proceed gradually, with many fine wear particles being generated concomitantly with large particles, spectroscopic oil analysis is quite adequate. However, for other applications, such as for highly loaded rolling element bearings, as are used in military aircraft gas turbines, fatigue failures generate only rather large particles as surface spalling begins. These surface defects then lead to further stress concentration in the bearing subsurface causing rapid surface breakdown and bearing failure. Conventional spectrometric oil analysis may not give adequate advanced warning for this type of failure.

A special type of optical emission spectrometer, called a Rotating Disk Electrode (RDE) spectrometer, is used by many military and commercial labs performing Spectrometric oil analysis. An inexpensive annular carbon disk electrode (called a "rotrode") is pressed onto the end of a rotatable shaft. A sample of lubricating oil is loaded into a sample cap and positioned so that the bottom of the carbon disk can be rotated through the oil sample. A capacitive spark gap is formed between the top of the disk and the tip of a carbon rod electrode. Oil that is carried by the disk from the cap to the tip of the rod electrode is vaporized, dissociated and excited to form a plasma. As in conventional optical emission spectroscopy, the wavelengths of light emitted during this burning are characteristic of the elements present in the oil sample; the light is directed to a spectrometer optic where the characteristic wavelengths of interest are quantified. A new carbon disk rotrode is used for each sample.

A technique called ferrography was developed in the early 1970's partly to address the inability of conventional optical emission spectroscopy to detect large particles in used lubricating oil samples. Ferrography is a magnetic separation technique that deposits wear particles on a glass substrate (called a ferrogram) for subsequent microscopic examination. Magnetic particles, i.e., ferrous particles, are deposited in an orderly fashion according to size. Other wear particles and contaminants are codeposited in a random fashion. The presence of codeposited contaminants may be detected, but they are not readily quantified.

A so-called Direct Reading or DR ferrograph was invented in the mid-1970's to make ferrography more quantitative. DR ferrography produces two readings which quantify the concentration of large ferrous particles and the concentration of small ferrous particles in an oil sample. The DR ferrograph is nonresponsive to nonferrous materials such as lead, tin, copper, aluminum, etc.

It is therefore an object of the present invention to provide a simple method of large particle measurement in a used oil sample for early failure detection/prediction in a condition monitoring/predictive maintenance program.

Conventional spectroscopy, including RDE spectroscopy, detects and quantifies small particle contaminants, generally below 1-5 micrometers, but is relatively insensitive to larger particles. Conventional ferrography, including the DR ferrograph, can quantify large particle concentration of contaminants in an oil sample, but is essentially limited to ferromagnetic materials.

It is therefore another object of the present invention to provide an improved RDE method and apparatus for spectrometric analysis of used oils for condition monitoring/predictive maintenance without the size or metal-type limitations of the prior art.

SUMMARY OF THE INVENTION

The present invention provides a highly accurate RDE spectroscopic method of evaluation of a fluid sample. One practice of the invention is based on a recognition that most abnormal wear modes cause an increase in concentration and size of wear particles and that early detection of large particles can provide early warning of impending equipment breakdown. This early detection is particularly useful for any equipment where in-use failure can be catastrophic.

In one aspect of the invention, large particles are captured on the surface of an RDE spectrometer rotrode, and the rotrode with the captured particles is then subjected to RDE spectroscopy to obtain a multi-elemental analysis of the captured particles. Such captured particles are measured essentially independently of, and not in the presence of, the dissolved and fine suspended particle contaminants of the oil sample, so as to provide a highly accurate multi-elemental determination of concentration of large particles in the oil sample.

In another aspect of the invention, such large-particle results are combined with the results of conventional RDE analysis of the dissolved and fine suspended particles in the sampled oil. Consequently, a complete wear analysis picture for an equipment of interest can be obtained.

In one embodiment of the invention, a rotating disk spectrometer apparatus has a rod electrode, a rotating shaft, and a rotrode disk for carrying particles loaded on its circumference, the disk disposed for mounting on the end of the shaft with a gap between the shaft and disk. Also included are means for loading the particles onto the disk circumference before the disk is mounted on the shaft, and adjustment means for adjusting the gap formed between the end of the rod and the disk circumference after the disk is mounted on the shaft. The rod and shaft are coupled to respective sides of a discharge circuit for generating a spark in the spark gap, wherein the rotating shaft rotates the particles loaded on the disk circumference through the spark for generation of a plasma for spectroscopic analysis.

In another embodiment of the invention, an RDE spectrometric apparatus includes cap means for capture of a portion of a porous disk electrode, cup means for capture of a second portion of the disk captured by the cap means, and vacuum means for drawing a sample fluid through the circumference of the carbon disk, wherein large particles in the sample fluid are captured on the disk circumference according to the porosity of the disk as the fluid is drawn through the disk.

In another embodiment of the invention, a method of evaluating a fluid sample by rotating disk electrode spectrometry includes flowing a fluid sample through the disk, and capturing particles from the sample on the disk circumference according to the porosity of the disk, and then submitting the particles captured on the disk circumference to spectroscopic analysis.

BRIEF DESCRIPTION OF THE DRAWINGS

These and other features and advantages of the present invention will be more fully understood by reference to the following detailed description in conjunction with the attached drawing in which like reference numerals refer to like elements and in which:

FIG. 1 is a schematic representation of an RDE spectrometer according to the invention.

FIG. 2 is a plan view of the rotrode filter of the invention.

FIG. 3 is a side-cross-sectional view of cap and cup devices of the invention.

FIG. 4 is shows the cap and cup of FIG. 3 in use.

DETAILED DESCRIPTION

Figure 5:
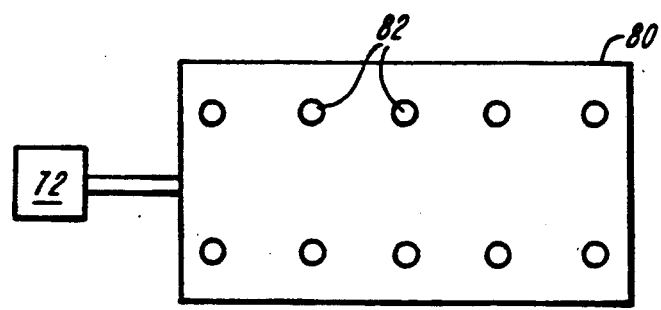
FIG. 5 is a plan view of a processing stand according to the invention.

Turning to FIG. 1, an RDE optical emission spectrometer 10 according to the invention is shown, and is operable for analysis of elements and/or contaminants in an oil sample. Spectrometer 10 forms a spark gap 12 between rotrode 14 mounted on splined mounting shaft 16 and the tip of rod electrode 18. The latter is mounted in electrode holder mechanism 20, which includes a mechanism for raising and lowering the rod 18 to adjust the size of gap 12. The rotrode 14 mounted via shaft 16 and the rod electrode 18 are coupled to a discharge circuit 21, and when this circuit is energized, a high energy spark is established at gap 12 between the electrodes.

A conventional RDE spectrometer includes a sample table 22 upon which a cup 24 having an oil sample 26 is mounted, and the conventional rotrode rotates through the oil in the cup and carries oil to the spark gap where rapid heating and vaporization generates a plasma, which in turn causes emission of light according to the elements present in the thus heated oil.

In practice of the invention, the conventional RDE spectrometer and method of use are modified, whereby a conventional RDE spectrometer carbon disk rotrode is used as a large particle filter, and is already loaded with the element sample before it is loaded into the spectrometer. Therefore, the conventional table 22 and cup 24 is obviated in practice of the present invention, and this is indicated by bracketing in FIG.1. The resulting apparatus 10 is simplified and yet more accurate than the conventional RDE equipment.

Apparatus 10 also includes quartz window and lens assembly 28 located adjacent spark gap 12, and which captures the plasma light emissions. Assembly 28, via fiber optic cable 30, couples the captured light emissions to an optical discriminator 32. Discriminator 32 separates the various spectra of interest, and readout system 34 converts the intensities of these spectra into electrical signals, which are processed into meaningful data for storage and later use or as immediate readouts at a display or printer 36. The readout device 36 indicates that elements, at different spectra and in specified quantities, have been detected.

In the preferred apparatus, the discriminator 32 takes the form of a polychromator based on the Rowland Circle concept. The light emissions carried by the optical fiber are focused on an entrance slit of the polychromator, which focuses an image onto a diffraction grating. The grating separates the light by diffraction into component wavelengths, and the light is distributed into discrete spectral lines. Precisely located exit slits pass specific wavelengths of interest. Readout system 34 preferably is a digital computer and accepts these wavelengths and produces meaningful output information. In the preferred embodiment, photomultiplier tubes precisely positioned at the exit slits of the polychromator convert the light passing therethrough into electrical signals, and these signals are processed and outputted to indicate presence and quantity of a detected element. The readout system preferably includes a digital computer and can be controlled by an input device 38, such as a keyboard.

A key aspect of the present invention is that the rotrode disk 14 is used as a filter. Thus a sample of oil is applied to the circumference of a conventional RDE spectrometer carbon disk rotrode and the sample is drawn through the disk, thus capturing large particles in the sample on the rotrode circumference. The rotrode 14 with the captured large-particle filtrate is then mounted on shaft 16 and subjected to RDE spectroscopy to obtain a highly accurate multi-elemental determination of concentration of large particles in the oil sample, such as for an early indication of equipment wear.

More specifically, as shown in FIG. 2, rather than conventionally placing oil sample 22 in cup 24 on stand 12, in practice of the present invention the large-sized particles 25 in the oil sample are isolated on the circumference 14' of disk 14 before the disk is loaded onto shaft 16. The amount of oil to be burned is substantially reduced, and a significant improvement in the sensitivity of the apparatus is thus obtained. In a particular embodiment of the invention, the disk filters particles approximately one micrometer and larger from the oil sample.

In a preferred embodiment of the invention, a cup 44 is used in conjunction with a cap 60 for capturing the sought-after large-sized particles 25 on the disk circumference 14'. As shown in the cross-sectional view of FIG. 3, cup 44 is formed on a hollow shaft 46, the upper interior tapered surface 47 of the cup defining a reservoir 48. The reservoir empties into an outlet 50 defined by the hollow shaft. A rim 52 defines the base of this reservoir and an o-ring 54 is captured in rim 52.

Cap 60 has a recessed surface 62 which is terminated by a rim 64. O-ring 66 is captured in rim 64. Rims 52 and 64 and o-rings 54 and 66 are of like dimensions, respectively. For each o-ring and rim combination, the inner diameter of the o-ring, as mounted in the rim, is slightly less than the outer diameter of disk 14. Therefore the disk can be mounted into each mounted o-ring by means of a pushing and twisting motion, with the disk 14 thereby captured between the cup 44 and cap 60.

As seen in FIG. 3, disk 14 is captured at its lower circumferential portion 68 within o-ring 54 and at its upper circumferential portion 70 within o-ring 66. O-ring 54 seals the disk lower circumferential portion 68 against fluid flow between the disk circumference 14' and the cup at rim 52. O-ring 66 seals the disk upper circumferential portion 70 against fluid flow between the disk circumference 14' and the surface of the cap at rim 64.

Carbon disk 14 is porous, and as a result of such sealed mounting of the disk to the cap and cup, when a vacuum is applied to hollow shaft 46 via vacuum source 72, an oil sample 74, shown in FIG. 4, poured into reservoir 48, will be drawn through the porous disk 14 and will drain through outlet 50 into the vacuum source discharge 77. Since the disk acts as a filter, it captures on its outer circumference 14' those particles which exceed the disk porosity. While some filtration occurs within the disk, it is the filtrate captured on the disk circumference that is subjected to spectroscopic analysis.

(It will be understood that FIGS. 3 and 4 show the cap and cup partially engaged for ease of description, while in use, the recessed surface 62 of the cap actually abuts the top surface of the captured disk.)

As shown in FIG. 2, the large particles 25 (filtered out of the oil sample) are captured on the disk circumference 14'. The filtered oil remainder is discarded. In order to accelerate the filtering period, the oil sample is preferably diluted with solvent. A preferred ratio is 1:1, for dilution of mineral base and synthetic oils with hexane.

The annular disk 14, at its interior diameter 14", is now mounted on shaft 16. (This mounting is done carefully so as to preserve the sample and to avoid contamination thereof; an extra splined shaft 16 can be used as a pickup tool.) RDE spectroscopy as described above is now performed on the rotating disk rotrode and an elemental analysis of the captured large contaminants is provided.

In a preferred method of the invention, the oil is washed from the collected large-sized particles, and therefore the ensuing analysis is carried out with a substantial, and almost complete, reduction in the amount of oil burned. This results in greater sensitivity in operation of the spectrometer, and reduced pollution emissions. More specifically, filtering of the diluted oil as described above is preferably followed, as shown in FIG. 4, by a solvent wash 76 poured into the reservoir 48 and drawn through the disk/filter 14, as indicated by arrow 75. As a result, the large particles of interest are captured on the surface of the disk with minimal or no oil residue.

Elimination of oil from the RDE spectroscopic evaluation has several benefits. For example, it reduces the energy required to vaporize the sample and also eliminates the oil from the plasma. This in effect presents a more concentrated particle sample to the plasma produced during RDE spectroscopy and leads to greater sensitivity of the RDE spectroscopy apparatus. As a result, a multi-elemental determination of the concentration of the large particles filtered out of the sample oil may be determined with great accuracy.

Thus, in practice of the invention, lower detection limits are obtainable compared to conventional RDE spectroscopy. This gain in sensitivity is quite probably a complicated function of particle size, shape, element type, etc.

We have experimentally determined that organo-metallic compounds which are routinely used as calibration standards for the RDE spectroscopic method (e.g., compounds such as "Conostan Standards", available from Conostan Division of Conoco Speciality Products, Inc., Ponca City, Okla.) are not captured by the rotrode when used in the process described herein. These organo-metallic compounds are of molecular size. This experimentation demonstrates that particles, but not dissolved material, are retained by the rotrode when used in the presently disclosed process.

Further experiments were performed upon chromium, nickel and molybdenum samples to demonstrate enhanced sensitivity of the invention as expressed by the limit of detection. According to our experiments, and based on the particular instrumentation upon which the experiments were performed (i.e., "Spectroil Jr." available from SPECTRO Incorporated, Littleton, Me.), a limit of detection of 0.71 ppm was determined in the normal method of operation of the equipment when calibrated with commercially available chromium organo-metallic standards (e.g., compounds such as "Conostan Standards," available from Conostan Division, Conoco Specialty Products, Inc., Ponka City Okla.), but in practice of the invention, when 1 ml of a 10 ppm suspension of commercially available powdered metal chromium particles in the 1 to 5 micrometer size range was filtered through a carbon disk electrode according to the invention, the limit of detection was determined to be 0.30 ppm for that equipment. As well, a limit of detection of 0.71 ppm was determined in the normal method of operation of the equipment when calibrated with commercially available nickel organo-metallic standards (e.g., "Conostan Standards"), but in practice of the invention, when 1 ml of a 10 ppm suspension of commercially available powdered metal nickel particles in the 1 to 5 micrometer range was filtered through a carbon disk electrode according to the invention, the limit of detection was determined to be 0.07 ppm. Finally, a limit of detection of 0.53 ppm was determined in the normal method of operation of the equipment when calibrated with commercially available molybdenum organo-metallic standards (e.g., "Conostan Standards"), but in practice of the invention, when 1 ml of a 10 ppm suspension of commercially available powdered metal molybdenum particles in the 1 to 5 micrometer size range was filtered through a carbon disk electrode, the limit of detection was determined to be 0.25 ppm.

The sensitivity of the invention can be further enhanced, i.e., the limit of detection can be further decreased, by virtue of the fact that the invention is integrative. To achieve a lower limit of detection, more sample may be filtered through the carbon disk electrode, thus capturing more particles which will result in greater instrument response.

Therefore, while one of the benefits of the present invention is provision of a simplified early detection method for condition monitoring/predictive maintenance, the above method and apparatus also enable a more sensitive test for large particle evaluation.

According to yet another method of the invention, the above filtering method is used to make a multi-elemental determination of the concentration of the large particles captured on the disk/filter, and then a second sample of the oil is subjected to conventional RDE spectroscopy for fine particle analysis. The combined results of these two tests gives total elemental content of the oil.

Preferably a plurality of samples are run at a given time so as to facilitate the efficient and reliable processing of a large number of samples by a given laboratory during a given work day. In order to facilitate such procedure, a vacuum stand 80 is provided having a plurality of receivers 82 for frictional or threaded receipt of shafts 46 of the cups 44. Thus a plurality of cups 44 are mounted on the stand and the same oil sample is prepared and filtered through respective disks under vacuum supplied by the vacuum source 72.

The above test is sensitive, and contamination of the rotrode should be avoided. For example, the cap and cup are preferably chrome plated brass, where copper or zinc contaminants rubbing from the brass onto the rotrode would be undesirable.

It will be understood that the above description pertains to only several embodiments of the present invention. That is, the description is provided by way of illustration and not by way of limitation. The invention, therefore, is to be limited according to the following claims.

What is claimed is:

1. A filtration apparatus for use in a spectrographic system, said apparatus comprising:
   a housing, said housing defining a vacuum port and means for capturing a bottom surface of a porous electrode disk having a central annulus, said capturing means including a port fluidly coupled with said annulus for hermetically capturing said disk;
   a device for drawing a particle-bearing fluid sample through an exposed circumference portion of the disk and depositing filtering particles thereon;
   said means for capturing further including a first device for capture of a first portion of the disk, and a second device for capture of a second portion of the disk, said first and second portions, cooperatively defining said exposed circumferential portion of said disk; and
   said drawing device further including a vacuum source for application of a vacuum to said disk for drawing said particle-bearing fluid sample through said exposed circumferential portion for separating particles from said fluid sample and leaving a filtrate on said exposed circumferential portion, said fluid being substantially removed from said exposed circumferential portion.

2. Apparatus of claim 1 wherein said first device includes a cap for capture of said first portion of said disk, and wherein said second device includes a cup for capture of said second portion of said disk, wherein particles in said fluid sample are captured as said filtrate when said fluid is drawn through said disk by said vacuum source.

3. Apparatus of claim 2 wherein the cap and cup each comprises a disk capture portion defining a rim.

4. Apparatus of claim 3 wherein the cup comprises a cylinder formed on a hollow shaft, the cylinder having an inwardly tapered top surface forming a reservoir, the base of the reservoir terminating in said hollow shaft, adjacent to said cup rim and wherein the cap comprises a cylinder having a recessed portion adjacent to said cap rim.

5. Apparatus of claim 4 further comprising a plurality of said caps and cups, and further comprising a stand having a plurality of receivers coupled to said vacuum source, the receivers for receipt of a respective one of said plurality of said cups, in a configuration wherein a vacuum supplied by said vacuum source to one of said cups mounted in respective one of said receivers will draw fluid through a respective disk captured between a respective cap and a respective cup for filtering the fluid.

6. In a rotating disk spectrographic system using a spectrometer apparatus having a rod electrode, a rotating shaft for rotation of an annular rotrode disk thereon, the rotrode disk for carrying particles loaded on its circumference, the disk disposed for mounting on the end of the shaft with a gap between the rod and disk, the rod and shaft for coupling to respective sides of a discharge circuit for generating a spark in said gap, the improvement comprising
   a filtration means, said filtration means defining a vacuum port and a device for capturing a bottom surface of the annular porous rotrode disk having a central annulus, the device including a port fluidly coupled with said central annulus for hermetically capturing said disk;
   a device for drawing a particle-bearing fluid sample through an exposed circumference portion of said disk and depositing filtered particles thereon; and
   means for rotating the disk and carrying the deposited particles through the spark in the gap for generation of a plasma for spectroscopic analysis.

7. The apparatus of claim 6 wherein said filtration means further comprises
   a first device for capture of a first portion of the disk, and
   a second device for capture of a second portion of the disk, the first and second portions defining the exposed circumferential portion of the captured disk, and
   a vacuum source for application of a vacuum to the captured disk for drawing the particle-bearing fluid sample through said exposed circumferential portion of the captured disk circumference and leaving thereon deposited particles, and
   said apparatus further comprising means for loading a preloaded disk on said shaft and for generation of said spark between said disk circumference portion and said electrode.

8. Apparatus of claim 7 wherein the first device includes a cap for capture of said first portion of the disk, and wherein the second device includes a cup for capture of said second portion of the disk, wherein particles in the sample fluid are captured on the disk circumference portion as the fluid is drawn through the disk.

9. Apparatus of claim 8 wherein the cap and cup each comprises a disk capture portion defining a rim.

10. Apparatus of claim 9 wherein the cup comprises a cylinder formed on a hollow shaft, the cylinder having an inwardly tapered top surface forming a reservoir, the base of the reservoir terminating in said hollow shaft adjacent to said cup rim.

11. Apparatus of claim 9 further comprising a plurality of said caps and cups, and further comprising a stand having a plurality of receivers coupled to said vacuum source, the receivers for receipt of a respective one of said plurality of said cups, in a configuration so that a vacuum supplied by said vacuum source to one of said cups mounted in respective one of said receivers will draw fluid through a respective disk captured between a respective cap and a respective cup for filtering the fluid.

12. A method of loading particles of at least a minimal size on a porous annular rotrode disk for RDE spectrometric analysis of a sample, comprising the steps of
    selecting a porous rotrode disk having a central annulus,
    placing the disk between a cap and an annular cup, a first interface of the cap and the disk forming a first seal, a second interface of the cup and the disk forming a second seal, the cap and the cup cooperating with the disk to define an exposed disk circumference between these interfaces,
    submitting the exposed disk circumference to a fluid sample and applying a vacuum from said annular cup to said central annulus of said disk and
    flowing the fluid sample through the exposed disk circumference toward the central annulus of said disk by applying said vacuum and capturing particles from the fluid sample on the exposed disk circumference, the minimal particle size collected on the exposed disk circumference being determined by the porosity of the disk.

13. The method of claim 12 further comprising the steps of
    providing a plurality of porous annular rotrode disks, a plurality of caps and cups,
    capturing each disk between a respective one of said plurality of caps and cups and forming a seal at each respective cap/disk interface and cup/disk interface, and respectively defining an exposed disk circumference between these interfaces on each said disk,
    submitting each exposed disk circumference to a fluid sample,and
    flowing a respective portion of the fluid sample through each exposed disk circumference toward the respective disk interior by applying a vacuum to the respective disk interior and capturing particles from the fluid sample on the respective exposed disk circumference.

* * * * *